US00RE46306E

(19) United States
(12) Reissued Patent
Bentley, II

(10) Patent Number: US RE46,306 E
(45) Date of Reissued Patent: Feb. 14, 2017

(54) FECAL IMPACTION REMOVAL TOOL

(71) Applicant: Centurion Medical Products Corporation, Williamston, MI (US)

(72) Inventor: Burton Bentley, II, Tucson, AZ (US)

(73) Assignee: Centurion Medical Products Corporation, Williamston, MI (US)

(21) Appl. No.: 14/168,464

(22) Filed: Jan. 30, 2014

Related U.S. Patent Documents

Reissue of:
(64) Patent No.: 8,105,335
Issued: Jan. 31, 2012
Appl. No.: 12/228,132
Filed: Aug. 11, 2008

(51) Int. Cl.
*A61B 17/22* (2006.01)
*A61M 29/00* (2006.01)
*A61M 1/06* (2006.01)

(52) U.S. Cl.
CPC ..... *A61B 17/22* (2013.01); *A61B 2017/22037* (2013.01); *A61M 29/00* (2013.01)

(58) Field of Classification Search
CPC ..... A61B 2017/22037; A61B 17/22; A61B 19/24; A61M 29/00
USPC .... 604/39, 104–106, 275–279, 514, 911, 73, 604/317, 48; 606/127, 128, 197, 198, 122, 606/124, 207
See application file for complete search history.

(56) References Cited

U.S. PATENT DOCUMENTS

| | | | | |
|---|---|---|---|---|
| 24,957 | A | 8/1859 | Shogren | |
| 833,759 | A * | 10/1906 | Sourwine | 604/105 |
| 1,383,502 | A * | 7/1921 | Vultee | 604/279 |
| 1,401,675 | A * | 12/1921 | Cooper | 604/279 |
| 1,737,488 | A * | 11/1929 | Zohlen | 606/197 |
| 1,828,986 | A * | 10/1931 | Stevens | 604/105 |
| 1,972,428 | A * | 9/1934 | Richard | 604/105 |
| 3,022,787 | A | 2/1962 | Daniel | |
| 3,459,175 | A | 8/1969 | Miller | |
| 3,659,611 | A * | 5/1972 | Miller | 128/207.15 |
| 3,842,834 | A * | 10/1974 | Vass | 604/278 |
| 3,889,676 | A | 6/1975 | Greene | |
| 3,894,539 | A * | 7/1975 | Tallent | 604/57 |
| 3,938,514 | A | 2/1976 | Boucher | |
| 4,014,332 | A * | 3/1977 | Sneider | 604/262 |
| 4,243,037 | A * | 1/1981 | Smith | 606/1 |
| 4,921,484 | A * | 5/1990 | Hillstead | 604/104 |
| 4,964,852 | A * | 10/1990 | Dunning et al. | 604/75 |

(Continued)

FOREIGN PATENT DOCUMENTS

| | | |
|---|---|---|
| AU | 200079397 A | 4/2001 |
| CA | 2261419 A1 | 8/2000 |
| DE | 2941743 A1 | 4/1981 |
| DE | 202004015357 U1 | 2/2005 |
| EP | 109897 A1 | 5/1984 |

(Continued)

*Primary Examiner* — Catherine S Williams
(74) *Attorney, Agent, or Firm* — Kristin L. Murphy; Brooks Kushman P.C.

(57) ABSTRACT

A manually manipulatable tool for removing a fecal impaction, the tool is adapted for insertion into a patient's rectum to engage and penetrate the impaction. The tool is fitted with flexible, arcuately configured elements collapsible at least partially during insertion into the rectum and penetration of the fecal impaction, withdrawal of the tool deploying the elements to exert traction on the impaction thus facilitating withdrawal of at least portions of the impaction. A body member of the tool is preferably elongated and can optionally be provided with a longitudinally extending lumen for introduction of an enema solution concurrently with or independently of impaction removal.

48 Claims, 5 Drawing Sheets

(56) References Cited

U.S. PATENT DOCUMENTS

| | | | | |
|---|---|---|---|---|
| 5,129,910 | A * | 7/1992 | Phan et al. | 606/127 |
| 5,702,404 | A | 12/1997 | Willingham | |
| 5,730,726 | A * | 3/1998 | Klingenstein | 604/105 |
| 5,827,304 | A | 10/1998 | Hart | |
| 5,976,170 | A | 11/1999 | Levin | |
| 6,138,984 | A | 10/2000 | Abell | |
| 6,395,021 | B1 * | 5/2002 | Hart et al. | 623/1.15 |
| 6,419,673 | B1 | 7/2002 | Edwards et al. | |
| 6,902,557 | B2 | 6/2005 | Mezzoli | |
| 8,016,816 | B2 | 9/2011 | Gregory | |
| 8,353,860 | B2 | 1/2013 | Boulais et al. | |
| 8,491,526 | B2 | 7/2013 | Cronin et al. | |
| 8,574,206 | B2 | 11/2013 | Bjerregaard et al. | |
| 8,579,857 | B2 | 11/2013 | Haack et al. | |
| 8,579,914 | B2 | 11/2013 | Menn et al. | |
| 2003/0130629 | A1 | 7/2003 | Cherepanov et al. | |
| 2005/0165412 | A1 | 7/2005 | Secrest et al. | |
| 2005/0197644 | A1 | 9/2005 | Waychoff, II | |
| 2005/0256464 | A1 | 11/2005 | Pallas | |
| 2007/0005001 | A1 | 1/2007 | Rowe et al. | |
| 2008/0045881 | A1 | 2/2008 | Teitelbaum et al. | |
| 2010/0042107 | A1 | 2/2010 | Merrifield | |
| 2011/0054413 | A1 | 3/2011 | Romhild et al. | |
| 2011/0092892 | A1 | 4/2011 | Nitsan et al. | |
| 2012/0253284 | A1 | 10/2012 | Nitsan et al. | |

FOREIGN PATENT DOCUMENTS

| | | | |
|---|---|---|---|
| EP | 0525110 | B1 | 4/1997 |
| WO | WO2008117320 | A1 | 10/2008 |
| WO | WO2011018092 | A1 | 2/2011 |
| WO | WO2012004118 | A1 | 1/2012 |

* cited by examiner

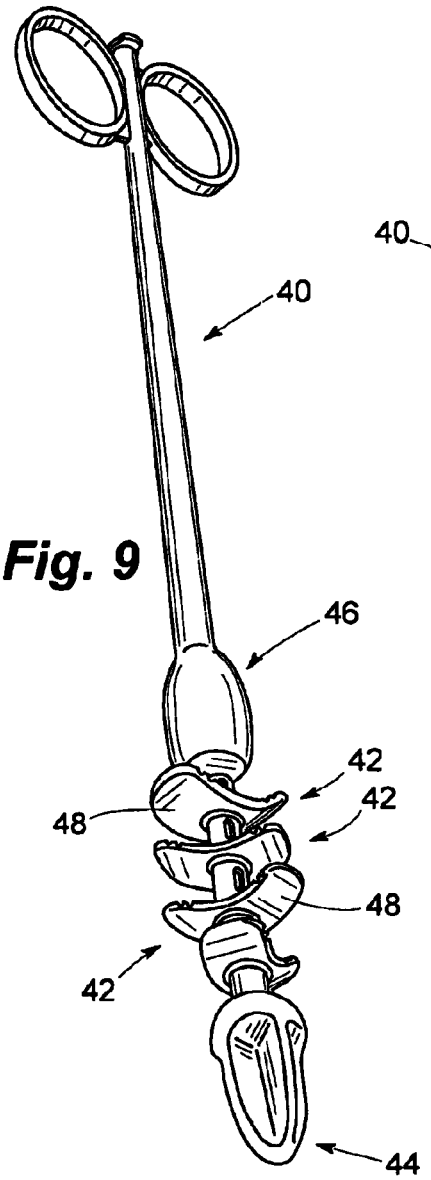
Fig. 9
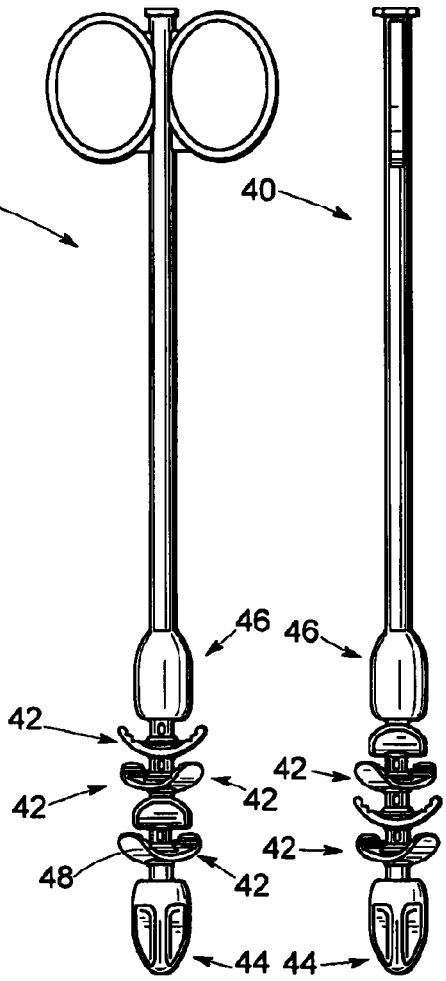
Fig. 10
Fig. 11
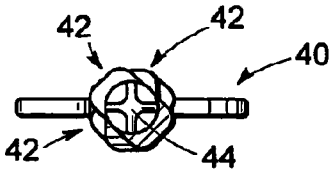
Fig. 12

FECAL IMPACTION REMOVAL TOOL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The invention relates generally to tools for removal of fecal impactions and particularly to such a tool configured for ease of useage and safety of operation for rapid and reliable removal of a fecal impaction.

2. Description of the Prior Art

Patients often present in clinical settings with impacted stools that can only be evacuated spontaneously with extreme difficulty if at all. Such blockages are typically referred to as fecal impactions and result from the inability to spontaneously empty the rectum of accumulated stool. A fecal impaction occurs due to excessive and continuing fecal mass accumulation in the rectal vault such that the large and growing fecal bolus cannot be readily passed through the anus. The impaction worsens as additional stool is produced and typically hardens with drying of distal portions of the impacted stool, thereby creating an increasingly uncomfortable and potentially dangerous emergency condition. Medical intervention is often required for removal of the impaction from the rectum especially once the density and mass of the accumulating stool precludes passage spontaneously.

While fecal impactions can occur in otherwise healthy individuals, those suffering from certain medical conditions including neuromuscular diseases and severe debilitation as well as those in the general geriatric population are susceptible to the spontaneous development of fecal impactions. Accordingly, fecal impaction is a commonly encountered condition in patients not only presenting in an emergency situation at a medical facility but also for patients hospitalized for other conditions.

Current clinical practice typically relies on repeated insertions of a finger of a medical practitioner through the anus and into the rectum of a patient for removal of the impaction. Practitioners called upon to accomplish this task include nurses, paramedics, medical technicians as well as physicians. As presently practiced, a clinician inserts a gloved finger through the patient's anus and into the rectum in an effort to manually dislodge the stool mass either entirely or in fragments. The gloved finger probes the fecal mass in an effort to break up the mass followed by retrieval of fragmented portions of the mass. The patient may become capable of spontaneous defecation once a sufficient portion of the mass has been removed manually. Removal of such sufficient portions or of the entire mass usually necessitates repeated manual interventions coupled with supplemental use of one or more fluid enemas. Hospital admission may be required for more intensive efforts to free an impaction.

Manual manipulation of an impacted fecal mass is subject to failure since utilization of a single, gloved finger weighs against application to the impaction of a mechanical advantage sufficient to relieve the condition. A finger is simply not configured to grasp the fecal mass or to gain attachment thereto due to the shape of a finger and the inability to frictionally engage the mass. Probing of the fecal mass with the finger of a clinician involves blind sweeps and stirring motions that are not easily directed advantageously and thus can prove ineffective. Patient discomfort is often increased by attempts of the attending clinician to curl the inserted finger in an effort to improve connection with the fecal mass. This flexion motion, though essential to the effort to grasp a portion of the fecal mass, causes further distention of an already distended bowel. Pain thus unavoidably accompanies inefficiency during attempts to remove the impaction and often results in the necessity to abort the procedure. Once an ineffective manual procedure is discontinued, hospitalization for repeated enema treatment becomes necessary with reliance then being placed on hydrodynamic dissolution of the impaction.

Such manual techniques while imperfect are commonly used in spite of the existence in the prior art of devices of varying complexity intended to address the task of fecal impaction removal. Examples of such devices include the apparatus disclosed by Klingenstein in U.S. Pat. No. 5,730,726, the disclosed apparatus comprising a shaft having flexible spines that can be bowed away from the shaft to engage the fecal mass after insertion into a patient's rectum. Smith, in U.S. Pat. No. 4,243,037, discloses a fecal impaction removal device comprising a plunger assembly adopted for introduction into the rectum of a patient and having prongs intended to engage an impacted fecal mass. In U.S. Pat. No. 3,316,912, Whitaker discloses a device insertable into the rectum followed by extension of a hinged scoop-like element intended to capture a portion of an impaction for removal. Sourwine, in U.S. Pat. No. 833,759, discloses a double loop handle connected to a distal and proximal dilator as well as expandable blade elements intended to permit more ready insertion and engagement of the impaction. Sims, in U.S. Pat. No. 1,448,158, discloses blades disposed closely along a shaft for insertion into the rectum with spreading of the blade after insertion to engage the fecal mass. The patents to Sourwine and Smith further disclose use of central channels in the respectively disclosed devices for introduction of enema solutions while said devices are contained within the rectal vault.

While fecal disimpaction devices have previously been suggested in the art, the art still experiences a need for a simple, inexpensive, safe and efficacious tool for removal of fecal disimpactions, the fecal disimpaction tool disclosed herein meeting these needs long-felt in the art through provision of a tool having distal and proximal dilators facilitating insertion into and withdrawal from the anus of a patient as well as flexible, arcuately configured finger-like elements formed of a flexible though non-elastic material collapsible against a central shaft during insertion and opening once within the rectal vault to engage the fecal mass for removal. The fecal disimpactor of the invention is shown to produce the functions and advantages thus referred to as is shown and described herein.

SUMMARY OF THE INVENTION

The invention provides a fecal impaction removal tool capable of use with maximum effectiveness and minimal patient discomfort. A preferred embodiment of the invention comprises an elongated shaft having a central lumen extending longitudinally therethrough, the lumen being provided proximally with a connection mechanism such as a Luer lock or similar coupling mechanism adapted for connection to a water jet or enema administration system that could comprise a syringe or the like. A handle such as can be comprised of twin loops can be integrally formed on the shaft adjacent the proximal opening of the lumen. The shaft of the tool terminates distally in a shaped dilator permitting ease of insertion into the anus of a patient suffering from a fecal impaction. A second dilator spaced from said first dilator along the shaft facilitates withdrawal of the tool from the patient, a series of flexible, arcuately configured grappling elements being disposed between the first and second dilators. The elements are preferably formed of a resinous material having a lower durometer relative to that of the resinous material forming the shaft, the dilator and remaining portions of the tool.

The grappling elements are shaped to cant backwardly from the first dilator and toward the second dilator, insertion of the tool into the anus of a patient causing the elements to compress inwardly behind the first dilator as the tool advances into the rectum to penetrate the fecal compaction. The tool is inserted sufficiently to cause the second dilator to be inserted through the anus of the patient so that the first and second dilators as well as the series of elements are disposed completely within the patient's rectal vault and have essentially pierced the fecal impaction. The tool can then be manipulated such as by twisting and by inward and outward movements of the tool short of withdrawal of the second dilator from the anus so that the impaction can be loosened and portions thereof can be fractured or subjected to a grasping action by the elements which extend outwardly of the shaft on manipulation such as can include partial back and forth movements of the tool within the rectal vault. Alternatively, the tool can simply be withdrawn after insertion as aforesaid thereby to cause outward extension of the elements and engagement between the elements and the fecal impaction prior to complete withdrawal of the tool through the patient's anus to thereby remove at least portions of the fecal impaction engaged with the elements and subject to loosening and fragmentation by the actions of the tool.

Practice of the invention can include use of the disimpaction tool more than once after cleaning. The use of more than one tool is desired since the procedure proceeds more rapidly if cleaning is not practiced. The tool of the invention is therefore preferably manufactured as a disposable item.

As noted herein, the shaft can be formed with a centrally disposed lumen terminating proximally in an opening adapted to be fitted with a conventional lock configured to be connected to a reservoir of enema fluids including gently pressurized fluid, fluid flow through the hollow shaft and exiting the shaft via ports located in the shaft between the first and second dilators resulting in contact between and entry of enema fluid into the fecal mass to facilitate loosening and fragmentation of the mass such that the grappling elements of the tool can grasp at least portions of the mass for removal.

Embodiments of the invention can conveniently be provided with three to four sets of the grappling elements, the sets of elements either being oriented identically along the shaft or rotated relative to adjacent sets to produce an interdigitated arrangement or even a "swirling" arrangement. The elements are preferably shaped with arcuate outer edges, each edge being disposed in opposing relation to the edge of said element located on the opposite side of the shaft. The elements are preferably formed with ridges extending at right angles to the shaft and disposed in proximity to edges of each element and on surfaces of the elements facing the proximal end of the tool, the ridges acting to engage the fecal mass more effectively. A reinforcing strut can be formed in each element set on proximal surfaces thereof and on portions of the elements on each side of the shaft. Pairs of ports communicating with the lumen of the hollow shaft are preferably formed in the shaft immediately proximally to each set of elements.

Accordingly, a primary object of the invention is to provide a reliable, inexpensive and easily and safely used tool for removing a fecal impaction, the tool having a shaped distal dilator facilitating insertion of the tool through the anus of a patient as well as for fragmentation of the impaction, the shaft being further formed with arcuately recurved grappling elements disposed proximally of the distal dilator and capable of compression toward the shaft during insertion and expansion into engagement with the impaction on full insertion into the rectal vault, the elements facilitating removal of at least portions of the impaction on removal of the tool through the patient's anus.

It is another object of the invention to provide a fecal impaction removal tool having a distal dilator and compressible or collapsible grappling elements located proximally of the dilator and formed on and with an elongated shaft, the shaft having an elongated lumen extending along the shaft from the anterior end of the shaft toward the distal dilator, the lumen being adapted to receive enema fluids therethrough, the fluids being vented from ports disposed near the distal dilator and into the fecal mass of the impaction to facilitate removal of the impaction.

It is a further object of the invention to provide a fecal impaction removal tool having a shaft, a handle disposed on a proximal end of the shaft to permit manipulation of the tool and sized to prevent loss of the tool into the rectal vault on insertion of the tool into the anus of a patient, and a distal dilator formed on the ends of the shaft opposite the handle, a proximal dilator also being formed on and with the shaft and spaced from the distal dilator, the shaft, the dilator and the handle being formed of a first relatively hard resinous "plastic" material and a series of compressible grappling elements formed on the shaft between the dilators and formed of a second "plastic" material of a reduced durometer or hardness relative to the durometer of the first material.

Further objects and advantages of the invention will become more readily apparent in light of the following detailed description of the invention.

BRIEF DESCRIPTION OF THE DRAWINGS

FIG. 9 is a perspective view of a second embodiment of the invention;

FIG. 10 is a side elevational view of the article shown in FIG. 9;

FIG. 11 is a side elevational view of the article seen in FIG. 10 and rotated ninety degrees about a longitudinal axis from the position seen in FIG. 10;

FIG. 12 is a plan view of the article seen in FIG. 9;

DESCRIPTION OF THE PREFERRED EMBODIMENTS

Figures 1, 2:
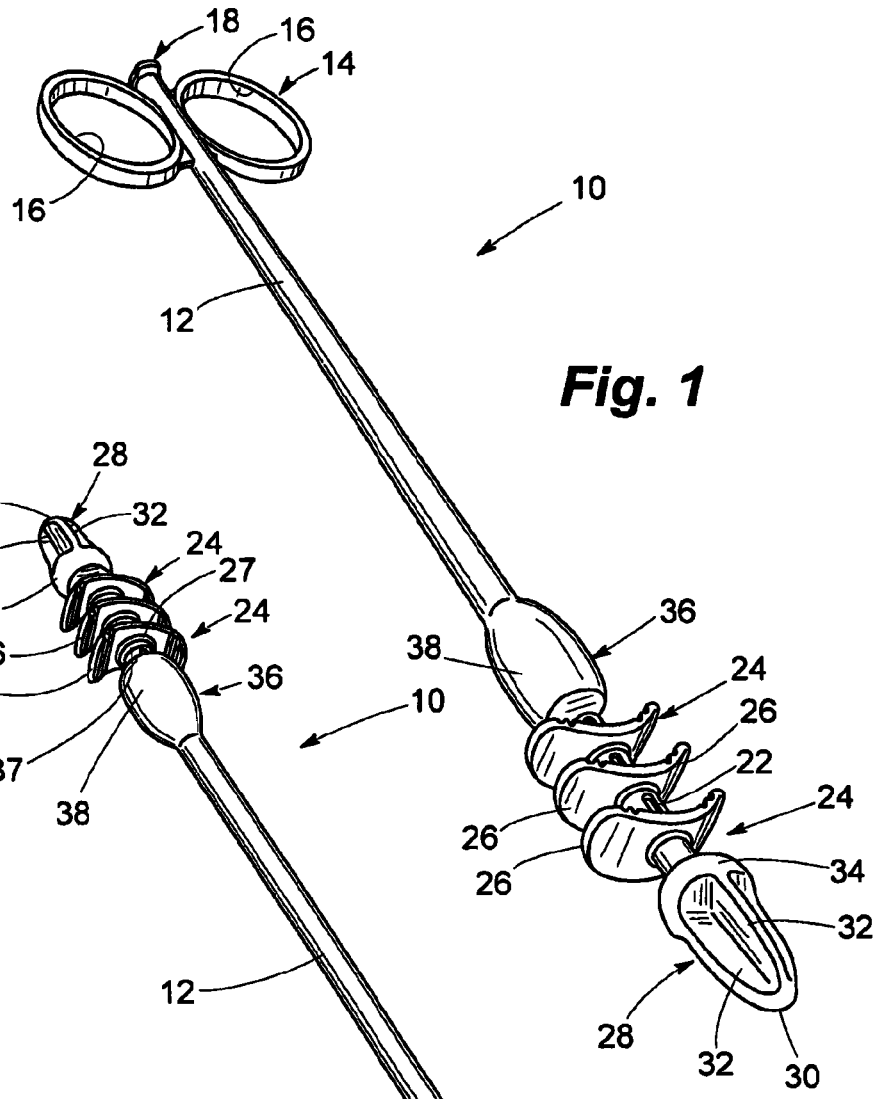
FIG. 1 is a perspective view of a first embodiment of the invention shown from a distal end of the invention.
FIG. 2 is a perspective view of the article shown in FIG. 1 seen from an anterior end.

Referring now to the drawings and particularly to FIGS. 1 through 8, a fecal impaction removal tool configured according to a first embodiment of the invention is seen at 10 to comprise an elongated shaft 12 preferably formed of a resinous or "plastic" material of a durometer imparting a desired rigidity such that a medical practitioner can insert distal portions of the tool 10 through the anus of a patient and into the rectal vault to engage an impacted fecal mass lodged therein. The flexible shaft 12 is sufficiently rigid to allow partial insertion of the tool 10 into the rectum as well as manipulation of the tool 10 while engaged with an impaction followed by withdrawal to remove at least fragments of an impaction created by manipulation of the tool 10.

The shaft 12 is terminated proximally by a handle 14 formed of loops 16 each capable of receiving one of a practitioner's fingers for ease of use of the tool 10 such as by application of torque to the tool 10 and especially for withdrawal of the tool 10 from the patient. The loops 16 are preferably formed integrally with the shaft 12 with each loop 16 being disposed in opposed relation in proximity to the proximal end of the shaft 12. The handle 14 is dimensioned to prevent entry of the entire tool 10 into the anus to prevent "loss" of the tool 10 into the rectum. As seen particularly in FIGS. 2 and 6, the shaft 12 terminates at it's proximal end in a locking adaptor 18 such as a conventional Luer lock. The locking adaptor 18 is disposed at the proximal end of a lumen 20 extending through the shaft 12 internally thereof thus forming a channel within the shaft 12 and causing the shaft 12 to be hollow through a substantial extent thereof from the proximal end inwardly toward a distal end of said shaft 12. The lumen 20 serves as a conduit for delivery of fluids such as enema fluids under pressure, the locking adaptor 18 facilitating connection to an apparatus (not shown) acting as a reservoir of such fluids with the unshown apparatus providing a capability to deliver enema fluids into the lumen 20. Such apparatus can comprise a syringe (not shown) or other device capable of secure coupling to the proximal end of the shaft 12 for delivery of an enema fluid into the lumen 20. The fluids thus introduced into the interior of the hollow shaft 12 are chosen for facilitation of stool softening, lubrication and/or mechanical absorption of an impacted fecal mass disposed in a patient's rectum. Such fluids can be introduced concurrently with or independently of manipulation of an impaction such as prior to intended manipulation.

Figure 3:
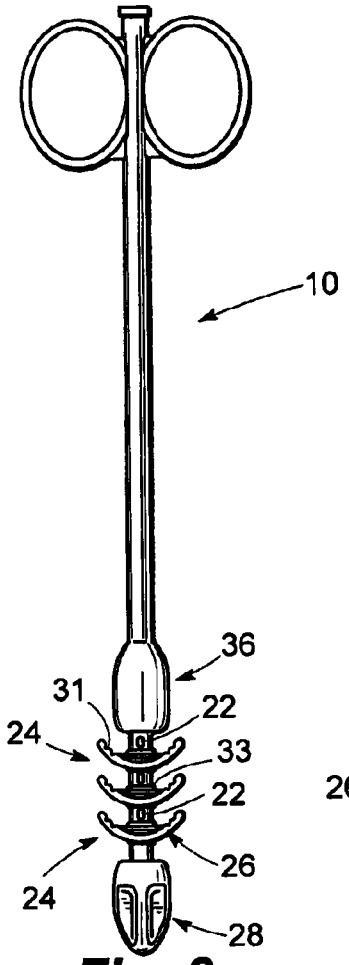
FIG. 3 is a side elevational view of the article seen in FIG. 1.
Figure 4:
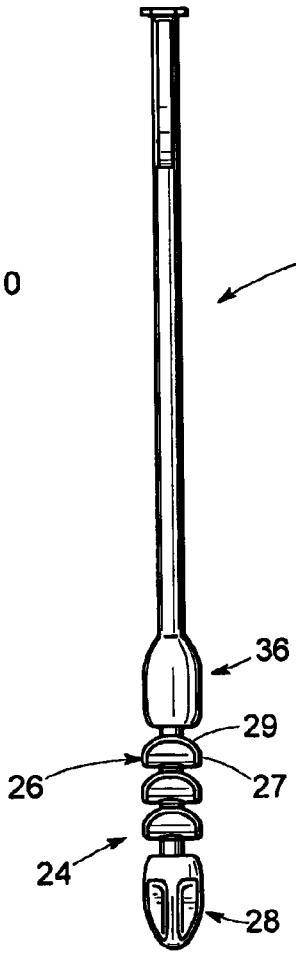
FIG. 4 is a side elevational view of the article seen in FIG. 3 and rotated ninety degrees about a longitudinal axis from the position seen in FIG. 3.
Figure 7:
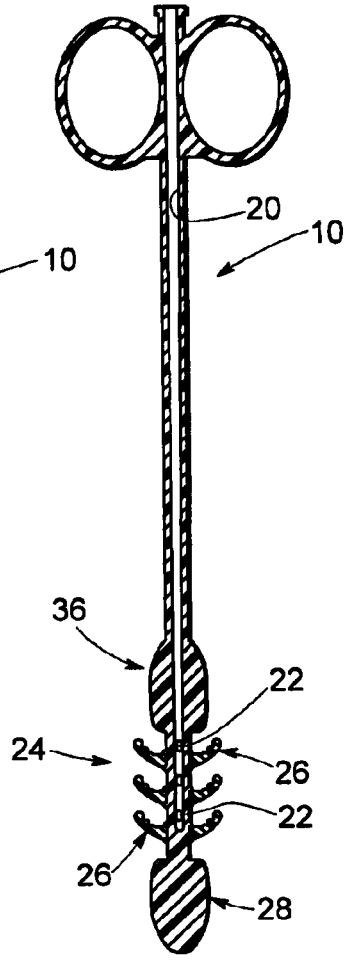
FIG. 7 is a side elevational view in section of the article as seen and as oriented in FIG. 3.
Figure 5:
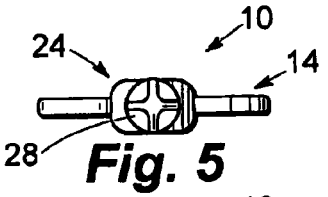
FIG. 5 is a plan view of the article seen in FIG. 1.
Figure 6:
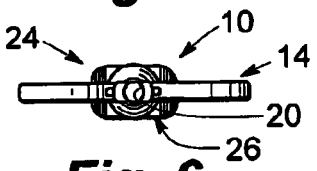
FIG. 6 is a bottom view of the article seen in FIG. 1.
Figure 8:
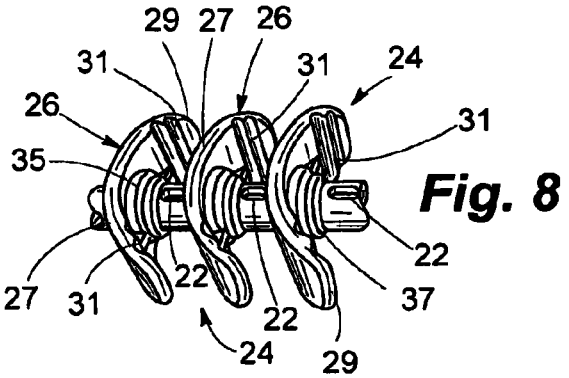
FIG. 8 is a detail perspective view of the article seen in FIG. 1.
Figure 13:
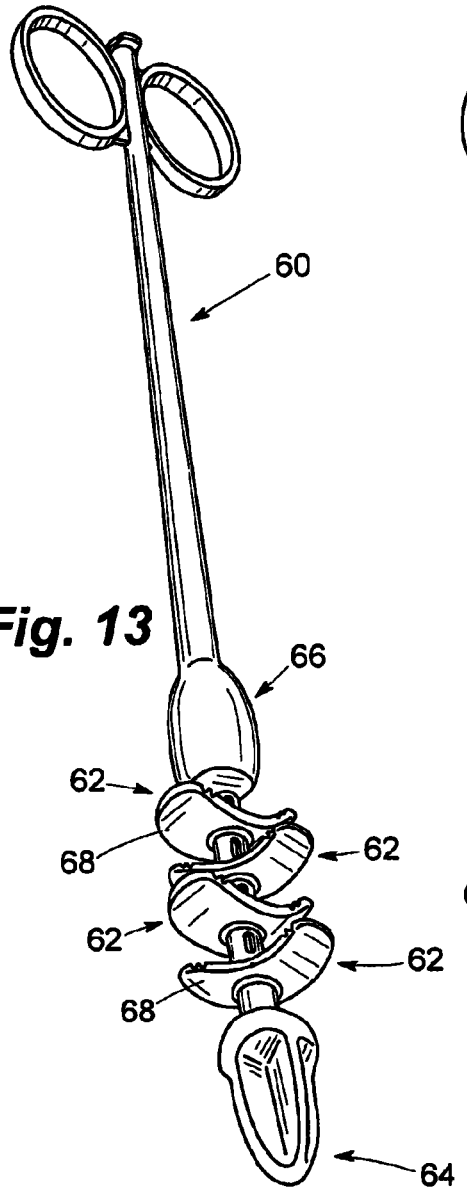
FIG. 13 is a perspective view of a third embodiment of the invention.
Figure 14:
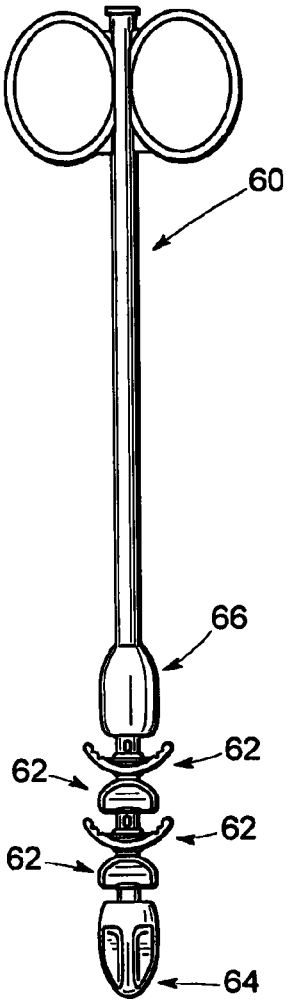
FIG. 14 is a side elevational view of the article shown in FIG. 13.
Figure 15:
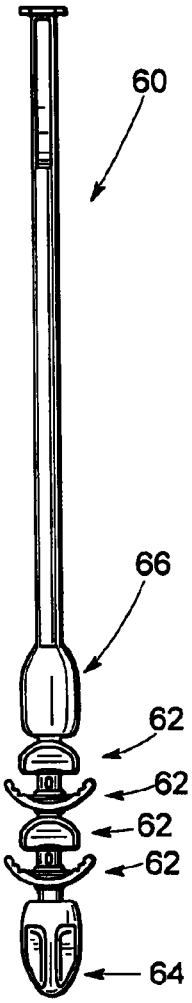
FIG. 15 is a side elevational view of the article seen in FIG. 14 and rotated ninety degrees about a longitudinal axis from the position seen in FIG. 14.
Figure 16:
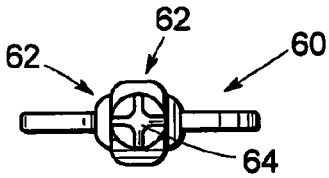
FIG. 16 is a plan view of the article seen in FIG. 13.
Figure 17:
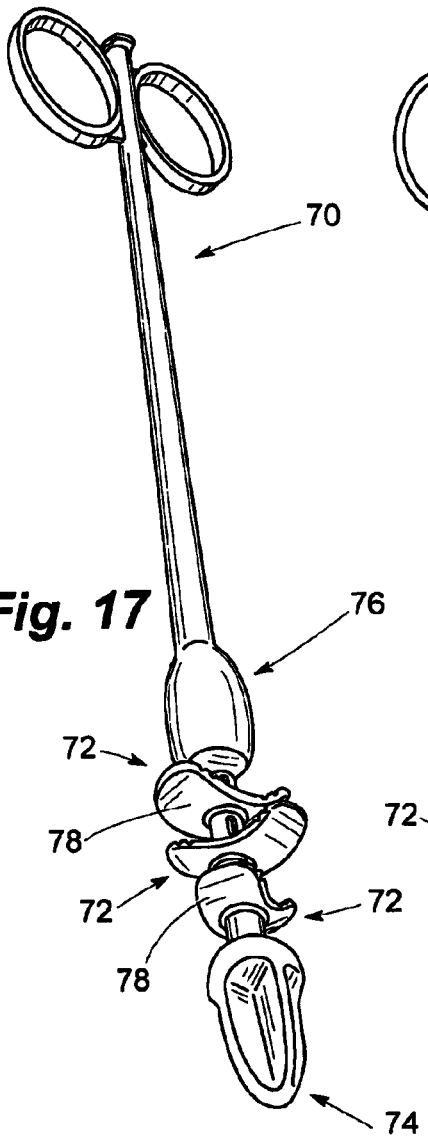
FIG. 17 is a perspective view of a fourth embodiment of the invention.
Figure 18:
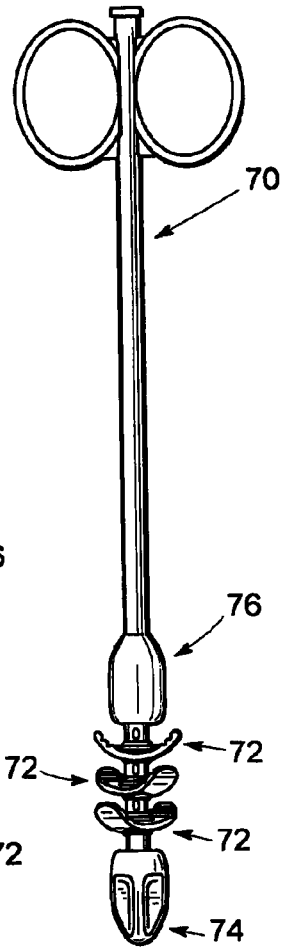
FIG. 18 is a side elevational view of the article shown in FIG. 17.
Figure 19:
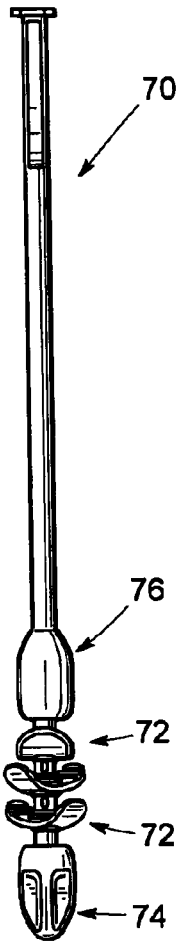
FIG. 19 is a side elevational view of the article seen in FIG. 18 and rotated ninety degrees about a longitudinal axis from the position seen in FIG. 18; and, FIG. 20 is a plan view of the article seen in FIG. 17.
Figure 20:
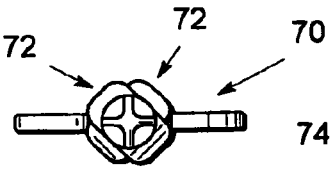

As is best seen in FIGS. 1, 3 and 8, the shaft 12 is formed with ports 22 disposed in spaced relation along the shaft 12 at locations along the shaft 12 near the distal end of said shaft. The ports 22 communicate the lumen 20 with an impaction or with the interior of the rectal vault so that enema solution introduced as aforesaid into the hollow shaft 12 is caused to contact an impacted fecal mass to facilitate softening and/or fragmentation of the mass either prior to or during manipulation of the tool 10 such as by application of torque by a practitioner manually grasping the loops 16 of the handle 12 and/or by a series of small inward and outward displacements of the tool 10. The ports 22 are typically formed in the shaft 12 in pairs with one each of the ports 22 in a pair of ports being located oppositely across the width or diameter of the shaft 12. As will be further described herein, the ports 22 are typically disposed immediately adjacent to and proximally of sets 24 of flexible, arcuately configured grappling elements formed on the shaft 12 as will be further described hereinafter.

The shaft 12 terminates distally in a first dilator 28 of a substantially ogive conformation with a rounded tip 30, the dilator 28 preferably being formed integrally with the shaft 12. The dilator 28 is formed distally in a cruciform configuration from a plurality of regularly spaced elements 32 that taper toward the tip 30 and join proximally to a substantially circular base 34 joined to the shaft 12. The elements 32 as well as surfaces of the base 34 are relieved, that is, essentially rounded such that the dilator 28 can be inserted into and withdrawn from a patient's anus with case and with minimal discomfort to the patient. The dilator 28 can be lubricated prior to insertion even though the material from which the dilator 28 as well as the shaft 12 inter alia is formed is chosen to exhibit low surface friction. The dilator 28 is shaped and sized such that insertion minimally distends an impacted fecal mass as well as the rectal vault to minimize patient discomfort.

A proximal dilator 36 is formed integrally with the shaft 12 in spaced relation to the distally disposed dilator 28. The dilator 36 is conically shaped proximally to facilitate removal of the tool 10 once manipulation of an impacted fecal mass has occurred. The dilator 36 can be formed with smooth, low friction surfaces over the exterior thereof and can be formed in a cruciform configuration as is the dilator 28 is formed distally except with such cruciform shape extending in the direction of withdrawal of the tool 10. The dilator 36 is intended to be received through the anus of a patient during insertion of the tool 10 and is therefore configured with an inwardly rounded annular shoulder 38 formed distally of the dilator 36. The dilator 36 configured as aforesaid facilitates the atraumatic withdrawal of the tool 10 through dilation of the anus and relaxation of the anal sphincter. Such relaxation and dilation permit withdrawal of at least portions of an impacted fecal mass engaged with the tool 10 with minimal effort and with minimal discomfort to the patient.

The shaft 12 of the tool 10 is further seen to be configured with spaced sets 24 of the flexible, arcuately configured grappling elements 26 disposed between the distally disposed dilator 28 and the proximal dilator 36. As is seen in FIGS. 1 through 8, the tool 10 is provided with three of the sets 24 while other drawings illustrate tools having three sets of grappling elements arranged in differing orientations as will be described hereinafter. The number of the sets 24 used in a particular tool configured according to the invention can vary and be other than is shown herein, the relative orientation between the sets 24 also varying as seen hereinafter and as is contemplated according to the invention.

Each of the grappling elements 26 comprising each one of the sets 24 can be identical and can comprise a substantially straight-edged inner body portion 27 having arcuate perimetric portions 29 at each end of said body portion 27. The elements 26 are preferably formed on and about the shaft 12 by co-extrusion of a "plastic" or resinous material of lesser durometer than forms the shaft 12 during formation of the tool 10. The material forming the elements 26 are thus preferably formed of a "softer" material to allow flexure of a sufficient degree to permit each element 26 of each arcuately-shaped set 24 to bend inwardly toward the shaft 12 on insertion of the tool 10 into the anus of a patient. The elements 26 can bend sufficiently to compress inwardly to positions wherein the perimetric portion 29 of each said element 26 virtually lies per se along the shaft 12 such that said element 26 need not create an entry path into the anus or into an impacted fecal mass. However, on full receipt into the fecal mass, compressing pressure on the elements 26 is either released due to restoring spring-like forces provided by the elements 26 per se and/or by manipulation of the tool 10 in one or more series of short inward and outward movements of the tool 10. The elements 26 during engagement with a fecal mass thus extend outwardly of the shaft 12 to positions similar to those existing prior to insertion. The fecal mass is thus engaged by the elements 26 in a "hooking" action and can be fragmented while embedded within the mass. Ridges 31 formed on rearwardly facing surfaces of the elements 26 act to increase retention of at least portions of the fecal mass on the tool 10.

As is best seen in FIG. 8, structural stability of the sets 24 is enhanced by integrally formed reinforcement struts 33 extending partially along a central axis of each of the elements 26 from the shaft 12. Further structural contributions are provided by concentric and congruent annuli 35 and 37 formed integrally with each set 24 on that side of said set facing proximally of the tool 10, the annulus 35 contiguous with the elements 26 being of greater diameter than the diameter of the annulus 37. Both of the annuli 35 and 37 are formed about the shaft 12 with the annulus 37 extending outwardly of the larger annulus 35 and being carried thereby. Clearly, these structural elements can be formed other than as explicitly shown.

Each set 24 of the elements 26 are seen to be oriented in an aligned relation to adjacent sets 24 as seen in FIGS. 1 through 8. As will be described hereinafter, the sets 24 can be otherwise oriented. The orientations herein shown as well as other orientations and numbers of the sets 24 contemplated by the invention function to produce the intended result of removal of fecal impactions.

Once the tool 10 has been inserted into the anus of a patient and manipulated to abduct the elements 26 from a position folded toward and along the body of the shaft 12 as is caused by insertion, the impacted fecal mass is engaged and then manipulated through manual movement of the handle 14 by a practitioner, these movements being translated along the shaft 12 to the opposite end of the tool 10 carrying the dilators 28 and 36 as well as the sets 24 of grappling elements 26. The length of the shaft 12 is chosen to be sufficient to efficiently permit insertion of the dilators 28 and 36 as well as the elements 26 and to effectively transmit forces exerted on the handle 14 to the distal end of the tool 10. It is to be understood that the grappling elements 26 can be formed in alternate embodiments of a sufficiently rigid material, such as the material forming the shaft 12, so that the sets 24 do not appreciably deform toward the shaft 12.

The pairs of the oppositely aligned ports 22 can best be seen in FIGS. 1, 3 and 8 to be disposed between adjacent sets 24 of the elements 26, the elements 26 collapsing in preferred embodiments on insertion of the tool 10 as aforesaid such that the ports 22 are shadowed by portions of said elements 26 and are thus protected from fecal occlusion by the collapse of a portion of said elements 26 over each port 22. However, fluid can exit the ports 22 while the elements 26 are collapsed thereover although abduction of the elements 26 after insertion permits pressurized fluid exiting the ports 22 to be more effectively directed against an impacted fecal mass.

Referring now to FIGS. 9 through 12, a second embodiment of the invention designated as tool 40 is seen to be essentially identical in all respects to the embodiment of FIGS. 1 through 8 with the exception of the relative orientation of sets 42 of grappling elements 48. The tool 40 is seen to be provided with distal and proximal dilators 44 and 46 respectively in a manner identical to the structure of the tool 10. However, the sets 42 and the grappling elements 48 are seen to be rotated angularly relative to each other by approximately 45° which, for a tool having four sets 42 of the grappling elements 48 as does the tool 40, produces a "swirling" arrangement of the sets 42. The functions of the tool 40 are essentially identical to the functions of the tool 10 shown in FIGS. 1 through 8 supra.

As is seen in FIGS. 13 through 16, a tool 60 is seen to be substantially identical to the tools 10 and 40 described herein with the common exception of the orientation of sets 52 of grappling elements 68. The tool 60 is provided with distal and proximal dilators 64 and 66 respectively as is common to the tools 10 and 40. However, the sets 62 of the grappling elements 68 are rotated at 90° angles relative to adjacent sets. The tool 60 is provided with four of the sets 62 as is seen best in FIGS. 13 through 15. The tool 60 functions as to results essentially identically to the function of the tools 20 and 40.

Referring now to FIGS. 17 through 20, a tool 70 is seen to be substantially identical to the tools described above with the exception of the orientation of sets 72 of grappling elements 78. The tool 70 is provided with distal and proximal dilators 74 and 76 respectively as is common to the tools described above. However, the second and third sets 72 of the grappling elements 78 from the tip of the tool 70 are rotated at 45 degree angles, the tool 70 having a total of three of the sets 72. A complete "footprint" of the sets 72 is seen to be provided by the use of three of the sets 72 rotated as shown in FIGS. 17 through 20. The tool 70 functions as to results essentially identically to the function of the tools described above.

While the invention has been described herein in relation to particular embodiments thereof, it is to be understood that the invention can be configured other than as explicitly disclosed and described herein. In practice, the elements 26 can be configured other than as described herein, varying configurations of the elements 26 contemplated by the invention being intended to connect to, grasp, clasp, dig into and/or engage with an impacted fecal mass as disclosed herein and being capable of formation other than as detailed herein. The articles of the invention can further be formed of differing materials consistent with the function of the articles or portions thereof without departing from the scope of the invention. Accordingly, the scope of the invention is to be interpreted in light of the appended claims.

What is claimed is:

1. An article of manufacture adapted for use in removal of a fecal impaction from a human being in need thereof and insertable into the rectum of said human being in need to manipulate the impaction, comprising:

a body member, at least a portion of which extends outwardly of the rectum of the human being experiencing an impaction on insertion of a distal portion of the body member into the rectum by a user, an outwardly extending anterior portion of the body member graspable by the user of the article to engage the impaction and to insert the distal portion of the article into the impaction;

at least one dilation body carried by the body member distally of said body member to facilitate entry of the body member into the rectum of the human being in need of removal of the impaction; [and,]

at least one grappling element carried by the body member on the distal portion of the body member and anteriorly of the at least one dilation body, the at least one grappling element for gripping at least portions of the impaction, at least one end of the at least one grappling element extending outwardly of the body member a distance greater than a volumetric space defined by passage of the at least one dilation body on insertion of the distal portion of the body member into the rectum, the volumetric space being defined by the at least one dilation body in an uncompressed condition prior to insertion into the rectum of a human being in need of removal of the impaction, the at least one grappling element being compressible toward the body member to a position essentially within the volumetric space, the grappling element being abducted from the body member within the rectum to grip at least portions of the impaction on sufficient insertion of the at least one grappling element into the rectum of the human being in need and to remove at least portions of the impaction on withdrawal of the body member from the rectum of the human in need of impaction removal*; and*

*a second dilation body carried by the body member and proximally disposed with respect to the at least one grappling element, the second dilation body having a tapered configuration tapering to a narrower proximal section;* wherein the at least one grappling element is arcuately formed in a relaxed and uncompressed condition and comprises an inner body portion joined to the body member and ends extending outwardly away from the body member, the ends of the at least one grappling element being more proximally disposed relative to body member than the inner body portion.

2. The article of manufacture of claim 1 and further comprising a handle disposed anteriorly of the body member, the handle being grasped by the user and the distal portion of the body member being manually inserted into the rectum of the human being in need of impaction removal, the at least one dilation body and the at least one grappling element being carried by the body member into the rectum with the at least one grappling element being inserted into the impaction and gripping at least portions of the impaction.

3. The article of claim 1 wherein the body member comprises an elongated shaft formed of a relatively rigid material and wherein the at least one grappling element is formed of a relatively less rigid material and is disposed at the end of the shaft insertable into the rectum of the human being in need of removal of the impaction.

4. The article of claim 3 wherein the shaft has a lumen extending from a proximal end thereof and toward a distal end of the shaft, the proximal end being adapted to receive into a proximal opening of the lumen a fluid capable of acting on the impaction.

5. The article of claim 4 wherein at least one port is formed in the shaft in proximity to the at least one grappling element, the port communicating with the lumen so that the fluid within the lumen can pass from the shaft into contact with the impaction.

6. The article of claim 4 and further comprising means carried at the proximal end of the shaft for connection to a source of the fluid.

7. The article of claim 2 wherein the handle comprises loops oppositely disposed across the body member near an anterior portion of the body member, each loop being adapted to receive at least one finger of the user and being formed integrally with the body member, the loops facilitating grasping of the article as well as movement and manipulation of the article.

8. The article of claim 3 wherein the at least one dilation body is disposed at the distal end of the shaft.

9. The article of claim 8 wherein the at least one dilation body is formed integrally with the shaft.

10. The article of claim 8 wherein the at least one dilation body is conformed into an ogive shape with a distal tip rounded to facilitate insertion of the at least one dilation body into the rectum of a human being in need of removal of the impaction.

11. The article of claim 10 wherein the at least one dilation body is comprised of tapered elements disposed in a cruciform conformation and tapering distally.

[12. The article of claim 8 and further comprising a second dilation body carried by the shaft in spaced relation to the distal end of the shaft, the second dilation body tapering proximally of the shaft to facilitate withdrawal of the article from the rectum of a human being in need of removal of the impaction.]

13. The article of claim [12] *1* wherein the second dilation body is formed integrally with the shaft.

14. The article of claim [12] *1* wherein the at least one grappling element is disposed on the shaft between the at least one dilation body disposed at the distal end of the shaft and the second dilation body.

15. The article of claim 8 wherein the at least one grappling element is carried by the shaft proximally of and substantially in proximity to the at least one dilation body disposed at the distal end of the shaft.

16. The article of claim 1 wherein the at least one grappling element is formed of a material having a lesser durometer relative to the durometer of the material forming the body member.

17. The article of claim 1 and further comprising at least one ridge element formed on a proximal face of the at least one grappling element, the at least one ridge acting to further engage the impaction.

18. The article of claim 1 and further comprising means for reinforcing the at least one grappling element.

19. The article of claim 1 wherein *the at least one grappling element comprises a plurality of grappling elements and* more than one of the grappling elements are carried by the body member in spaced relation to each other.

20. The article of claim 19 wherein longitudinal axes of body portions of adjacent grappling elements are aligned relative to each other.

21. The article of claim 19 wherein longitudinal axes of body portions of adjacent grappling elements are angularly disposed relative to each other.

22. The article of claim 21 wherein longitudinal axes of body portions of adjacent grappling elements are disposed at 90° angles to each other.

23. The article of claim 19 wherein at least three of the grappling elements are carried by the body member.

*24. An article of manufacture adapted for use in removal of a fecal impaction from a human being in need thereof and insertable into the rectum of said human being in need to manipulate the impaction, comprising:*

*a body member, at least a portion of which extends outwardly of the rectum of the human being experiencing an impaction on insertion of a distal portion of the body member into the rectum by a user;*

*a distally disposed tip portion of said body member to facilitate entry of the body member into the rectum of the human being;*

*at least one grappling element carried by the body member on the distal portion of the body member,*

*a lumen disposed within the body member and extending to the at least one grappling element and capable of delivering fluid to the at least one grappling element;*

*at least one dilation body carried by the body member and proximally disposed with respect to the at least one grappling element, the dilation body having a tapered configuration tapering to a narrower proximal section;*

*each grappling element being compressible toward the body member and abducted from the body member within the rectum to grip at least portions of the impaction on sufficient insertion of the at least one grappling element into the rectum of the human being, and to remove at least portions of the impaction on withdrawal of the body member from the rectum of the human in need of impaction removal;*

*each grappling element extending outwardly of the body member a distance greater than a volumetric space defined by the at least one dilation body in an uncompressed condition;*

*wherein each grappling element is arcuately formed in a relaxed and uncompressed condition and comprises an inner body portion joined to the body member and an outer portion including a pair of opposed ends extending outwardly away from the body member, the ends of the at least one grappling element being more proximally disposed relative to the body member than the inner body portion.*

*25. The article of manufacture of claim 24, wherein the at least one grappling element comprises a plurality of grappling elements aligned along a longitudinal axis, the opposed ends of the grappling element each extend in a direction transverse to the body member and the plurality of grappling elements are aligned such that the opposed ends of adjacent grappling elements are rotated with respect to one another.*

*26. The article of claim 24 wherein each grappling element is compressible to a first insertion position adjacent to the body member.*

*27. The article of claim 26 wherein each grappling element has an unbiased position between the first insertion position and a second engaging position in the uncompressed condition, and wherein the grappling element moves from the unbiased position to the first insertion position upon insertion of the article.*

*28. The article of claim 27 wherein the unbiased position is a position with the outer portion extending toward the proximal portion of the body member.*

*29. The article of claim 24 wherein the at least one grappling element is formed of a resiliently flexible material.*

*30. The article of claim 24 wherein the at least one grappling element includes a proximal surface and a distal surface, the proximal surface configured to increase retention of at least portions of the impaction with the article during removal.*

*31. The article of claim 30 wherein the proximal surface includes a structural element configured to increase retention of at least portions of the impaction with the article during removal.*

*32. The article of claim 31 wherein the structural element is a ridge configured to increase retention of at least portions of the impaction with the article during removal.*

*33. The article of claim 29 wherein the at least one grappling element includes a surface and a reinforcement element on the surface extending radially outward from the body member configured to restrict flexure of the at least one grappling element.*

*34. The article of claim 24 wherein the tip portion includes a further dilation body to facilitate entry of the body member into the rectum of the human being, the further dilation body extending radially outward from the body member.*

*35. The article of claim 34 wherein the further dilation body is formed integrally with the body member.*

*36. The article of claim 34 wherein the further dilation body is comprised of elements disposed in a cruciform conformation.*

*37. The article of claim 34 wherein the further dilation body includes a base, and tapers distally from the base to facilitate the insertion of the distal end into the rectum of a human being and to minimally distend the impaction for minimal patient discomfort during insertion.*

*38. The article of claim 24, wherein the at least one dilation body includes a shoulder and tapers proximally from the shoulder to facilitate the automatic withdrawal of the distal end from the rectum of a human being.*

*39. The article of claim 34 wherein an engaging position of the grappling elements in the uncompressed condition includes the opposed ends extending radially beyond a radial extent of the further dilation body to engage at least a portion of the impaction.*

*40. The article of claim 24 wherein the lumen extends from the proximal portion toward the distal portion and includes one or more ports formed in the distal portion configured to allow fluid to pass from the lumen to contact at least portions of the impaction, the proximal portion including an opening adapted to receive a fluid capable of acting on the impaction, at least one port having a radial opening.*

*41. The article of claim 40, wherein the at least one port is disposed adjacent a grappling element of the at least one grappling element, configured to protect said port from occlusion during insertion of the article.*

*42. The article of claim 24 wherein the proximal portion comprises a handle graspable by a user.*

*43. The article of claim 24 wherein the at least one grappling element comprises a plurality of grappling elements aligned along a longitudinal axis including a first grappling element and a second grappling element longitudinally displaced from the first grappling element, the second grappling element rotated angularly around the longitudinal axis relative to the first grappling element.*

*44. The article of claim 26 wherein the at least one grappling element comprises a plurality of grappling elements formed of a resiliently flexible material and aligned along a longitudinal axis, each grappling element having an unbiased position between the first insertion position and a*

*second engaging position, wherein the unbiased position is a position with the outer portion extending toward the proximal portion of the body member, and each grappling element moves from the unbiased position to the first insertion position upon insertion of the article, wherein the plurality of grappling elements include a first grappling element and a second grappling element longitudinally displaced from the first grappling element, the second grappling element rotated angularly around the longitudinal axis relative to the first grappling element.*

*45. The article of claim 44 wherein each grappling element includes a proximal surface having a structural element configured to increase retention of at least portions of the impaction with the article during removal.*

*46. The article of claim 45 wherein the lumen extends from the proximal portion toward the distal portion and includes a plurality of ports formed in the distal portion configured to allow fluid to pass from the lumen to contact at least portions of the impaction, the proximal portion including an opening adapted to receive a fluid capable of acting on the impaction, each port having a radial opening.*

*47. A method for engaging a fecal impaction in a human being with an article of manufacture adapted for use in removal of a fecal impaction from a human being in need thereof, comprising the steps of:*

*providing a fecal impaction removal article including a body member, at least a portion of which extends outwardly of the rectum of the human being experiencing an impaction on insertion of a distal portion of the body member into the rectum by a user; a distally disposed tip portion of the body member to facilitate entry of the body member into the rectum of the human being; at least one grappling element carried by the body member on the distal portion of the body member, a lumen disposed within the body member and extending to the at least one grappling element and including ports capable of delivering fluid to the at least one grappling element; at least one dilation body carried by the body member and proximally disposed with respect to the at least one grappling element, the dilation body having a tapered configuration tapering to a narrower proximal section; each grappling element being compressible toward the body member, each grappling element extending outwardly of the body member a distance greater than a volumetric space defined by the at least one dilation body in an uncompressed condition; each grappling element being abducted from the body member within the rectum to grip at least portions of the impaction on sufficient insertion of the at least one grappling element into the rectum of the human being, and to remove at least portions of the impaction on withdrawal of the body member from the rectum of the human in need of impaction removal, wherein each grappling element is arcuately formed in a relaxed and uncompressed condition and comprises an inner body portion joined to the body member and a pair of opposed ends extending outwardly away from the body member, the ends of the at least one grappling element being more proximally disposed relative to the body member than the inner body portion;*

*inserting the distal portion into the rectum of the human being with a fecal impaction until at least one of the ports is disposed in a portion of the impaction;*

*delivering fluid through the lumen and through at least one of the ports having a radial opening to direct fluid to contact at least an internal portion of the impaction with the fluid and to loosen the impaction; and*

*removing the distal portion from the rectum of the human being while causing the at least one grappling element to engage and remove portions of the loosened impaction.*

*48. The method of claim 47 wherein the delivering fluid includes delivering fluid to a plurality of the ports to direct fluid radially from the shaft to contact a plurality of portions of the impaction concurrently with the fluid.*

*49. The method of claim 47 wherein the at least one grappling element comprises a plurality of grappling elements disposed at different locations along a longitudinal axis and further comprising causing the grappling elements to cover and protect the ports during insertion and causing the grappling elements to extend away from the ports before delivering fluid.*

* * * * *